United States Patent [19]
Komurasaki

[11] Patent Number: 4,949,571
[45] Date of Patent: Aug. 21, 1990

[54] ACCELERATION DETECTOR

[75] Inventor: Satoshi Komurasaki, Himeji, Japan

[73] Assignee: Mitsubishi Denki Kabushiki Kaisha, Tokyo, Japan

[21] Appl. No.: 389,469

[22] Filed: Aug. 4, 1989

[30] Foreign Application Priority Data

Aug. 5, 1988 [JP] Japan .................. 63-103203[U]

[51] Int. Cl.⁵ .............................................. G01H 11/08
[52] U.S. Cl. .......................................... 73/35; 73/654; 73/431; 310/329
[58] Field of Search ............... 73/35, 654, 517 R, 431; 310/329

[56] References Cited

U.S. PATENT DOCUMENTS 4,326,143  4/1982  Guth et al. .................. 310/329
4,399,705  8/1983  Weiger et al. ................. 73/654
4,885,439  12/1989 Otsubo ...................... 200/61.45 R Primary Examiner—John Chapman
Attorney, Agent, or Firm—Sughrue, Mion, Zinn, Macpeak and Seas

[57] ABSTRACT

An acceleration detector comprising a housing defining a cavity therein and including a metallic bushing and a resinous outer case. An acceleration transducer assembly is disposed on the bushing in the cavity, and a resilient filler material is applied around the acceleration transducer assembly for resiliently sealing the acceleration transducer assembly from the exterior. The resilient filler material is sufficiently resilient to allow the movement of the inertial weight relative to the housing when an acceleration is applied to the inertial weight. The metallic bushing and the resinous outer case are integrally attached together by insert-molding so that they become an integral structure.

3 Claims, 1 Drawing Sheet

FIG. I
PRIOR ART
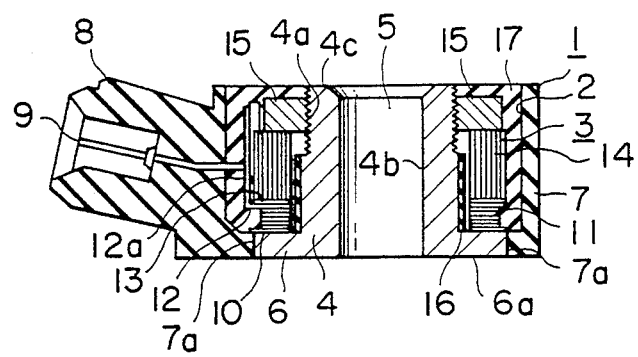
FIG. 2
PRIOR ART
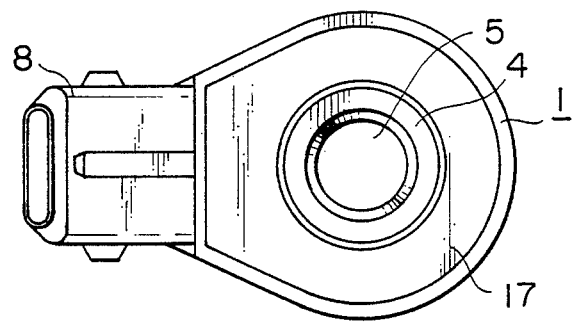
FIG. 3
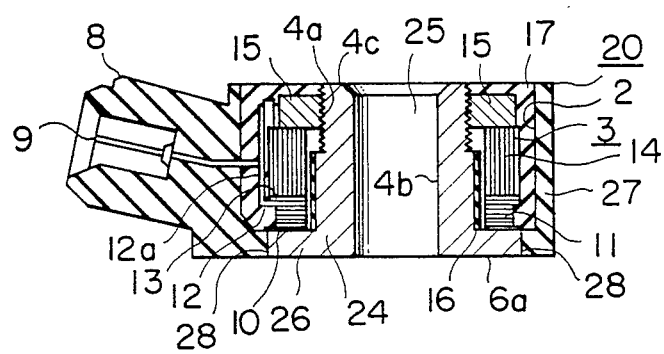

ACCELERATION DETECTOR

BACKGROUND OF THE INVENTION

This invention relates to an acceleration detector an more particularly to an acceleration detector for detecting knocking in an internal combustion engine.

FIGS. 1 and 2 illustrate one example of an acceleration detector to which the present invention can be applied. The acceleration detector comprises a housing 1 defining an annular cavity 2 therein and an annular acceleration transducer assembly 3 disposed within the cavity 2. The housing 1 comprises a tubular, electrically conductive metallic bushing 4 having a through hole 5 and a flange 6. The housing 1 also comprises a ring-shaped resinous outer case 7 bonded by a bonding agent 7a to the flange 6 of the bushing 4 so that the cavity 2 is defined therein.

The outer case 7 also has a connector 8 radially outwardly extending from the outer case 7 so that an output terminal 9 can extend through the connector 8 for taking out an output signal from the acceleration transducer assembly 3 disposed within the cavity 2. The acceleration transducer assembly 3 further includes an annular piezoelectric element 11 placed on the terminal plate 10, a washer-shaped terminal 12 including a lead 12a connected to the output terminals 9, an electrically insulating washer 13 disposed on the washer terminal 12, an annular inertial weight 14 placed on the insulating washer 13 and a threaded ring-shaped stop nut 15 thread-engaged with the thread 4a on the tubular bushing 4. An electrically insulating tape or tube 16 is placed on the tubular bushing 4 so that the acceleration transducer assembly 3 is insulated from the bushing 4 even when the washer terminal 12 as well as the piezoelectric element 11 are eccentrically assembled.

In order to resiliently support and protect the acceleration transducer assembly 3 within the cavity 2 from undesirable environmental conditions, the remaining space of the cavity 2 of the housing 1 which is not occupied by the acceleration transducer assembly 3 is substantially filled with a resilient filler material 17 of a thermo-setting resin. The filler material 17 must be sufficiently resilient after it is cured to allow the movement of the inertial weight 14 relative to the housing 1 when an acceleration is applied to the inertial weight 14 so that the piezoelectric element 11 generates a voltage signal proportional to the pressure exerted on it by the relative movement of the inertial weight 14 against the piezoelectric element 11.

When in use, the acceleration detector is securely mounted on the internal combustion engine (not shown) by a suitable bolt (not shown) inserted into the central through hole 5 of the housing 1. The acceleration or the vibration of the internal combustion engine produces the movement of the inertial weight 14 relative to the housing 1, which causes the piezoelectric element 11 to be stressed by the inertial weight 14, whereby an electrical signal indicative of the movement of the inertial weight 14 relative to the engine is generated from the piezoelectric element 11. The electrical signal is provided from the output terminal 9 to be analyzed to determine as to whether or not a knocking signal which generates upon knocking of the internal combustion engine is involved. When it is determined that a knocking signal is contained in the electrical signal, the operating parameters for operating the engine can be adjusted to increase the output power or decrease the fuel consumption rate.

In the conventional acceleration detector as above described, since the metallic bushing 4 and the outer case 7 are bonded by the bonding agent 7a at the bottom wall of the housing 1 and a heat must be applied to the bonding agent 7a for the purpose of drying the bonding agent 7a, the metallic plating on the bushing is deteriorated by the applied heat, degrading the corrosion resistance of the plating. Also, since the application amount of the bonding agent cannot be easily controlled due to the difficulty in adjusting the preheating and supplying pressure of the bonding agent during application, the excess amount of the bonding agent can often be applied. Therefore, the bonding agent may coat the inner surface of the bushing which should be brought into a good electrical contact with the transducer assembly. This excess amount of the bonding agent sags and runs also onto the bottom surface of the housing 1 which should be smooth and electrically conductive, degrading the reliability of the acceleration detector. Further, it is very difficult to remove the excess amount of bonding agent hardened on the inner and outer surfaces of the housing 1.

SUMMARY OF THE INVENTION

Accordingly, one object of the present invention is to provide an acceleration detector free from the above discussed problems.

Another object of the present invention is to provide an acceleration detector in which no bonding agent is used between the metallic bushing and the resin outer case.

A further object of the present invention is to provide an acceleration detector in which an insertion molding is used to firmly connect the metallic bushing and the resin outer case.

With the above objects in view, the acceleration detector of the present invention comprises a housing defining a cavity therein and including a metallic bushing and a resinous outer case. An acceleration transducer assembly is disposed on the bushing in the cavity, and a resilient filler material is applied around the acceleration transducer assembly for resiliently sealing the acceleration transducer assembly from the exterior. The resilient filler material is sufficiently resilient to allow the movement of the inertial weight relative to the housing when an acceleration is applied to the inertial weight. The metallic bushing and the resinous outer case are integrally attached together by insert-molding so that they provide an integral unitary structure.

BRIEF DESCRIPTION OF THE DRAWINGS

The present invention will become more readily apparent from the following detailed description of the preferred embodiments of the present invention taken in conjunction with the accompanying drawings, in which:

FIG. 1 is a sectional view showing one example of a conventional acceleration detector in which the metallic bushing and the resin outer case are bonded together by the bonding agent;

FIG. 2 is a plan view of the acceleration detector shown in FIG. 1; and

FIG. 3 is a sectional side view of the acceleration detector of the present invention in which the metallic bushing is integrally molded within the resin outer case.

DESCRIPTION OF THE PREFERRED EMBODIMENTS

FIG. 3 illustrates an acceleration detector 20 of the present invention. The acceleration detector 20 comprises a housing 1 defining an annular cavity 2 therein and an annular acceleration transducer assembly 3 disposed within the cavity 2. The housing 1 comprises a tubular, electrically conductive metallic bushing 24 having a through hole 25 and a flange 26. The housing 1 also comprises a ring-shaped risinous outer case 27 attached to the flange 26 of the bushing 24 so that the cavity 2 is defined therein. According to the present invention, the metallic bushing 24 and the resinous outer case 27 are attached to each other at the interface 28 not by a bonding agent as in the conventional design shown in FIGS. 1 and 2, but by insertion molding in which the bushing 24 is embedded in the integrally molded resin material of the outer case 27. The outer case 27 is preferably made of a fluorocarbon resin and polybutyleneterephthalate.

In other respects, the acceleration detector 20 of the present invention is identical to the conventional acceleration detector shown in FIGS. 1 and 2, so that their description will not be repeated.

According to the acceleration detector of the present invention, the metallic bushing and the resinous outer case are integrally joined together by insert-molding to provide an integral unitary structure. Therefore, no bonding agent is necessary, thereby removing the disadvantages of the conventional design using the bonding agent as previously described. That is, the metallic plating on the bushing is not deteriorated by the applied heat for curing, maintaining the necessary corrosion resistance of the plating. Also, the inner and outer surfaces of the bushing and case can be kept clean, enabling to establish a good electrical contact with the transducer assembly and the grounding member, thus increasing the reliablity of the detector.

Moreover, since the attachment of the bushing to the outer case is simultaneously achieved during the insert-molding of the case, the number of manufacturing steps can be reduce. Also, the productivity is increased and the manufacturing cost can be reduced.

What is claimed is:

1. An acceleration detector comprising:
   a housing defining a cavity therein and including an electrically conductive metallic bushing and an electrically insulating resinous outer case:
   an acceleration transducer assembly disposed on said bushing in said cavity; and
   a resilient filler material applied around said acceleration transducer assembly for resiliently sealing said acceleration transducer assembly from the exterior, said resilient filler material being sufficiently resilient to allow the movement of said inertial weight relative to said housing when an acceleration is applied to said inertial weight;
   said metallic bushing and said resinous outer case being integrally attached together by insert-molding to provide an integral structure.

2. An acceleration detector as claimed in claim 1, wherein said metallic bushing is metal plated.

3. An acceleration detector as claimed in claim 1, wherein said outer case is made of a resin material selected from a group consisting of a fluorocarbon resin and polybutyleneterephthalate.

* * * * *